(12) United States Patent
Fenech et al.

(10) Patent No.: US 11,284,950 B2
(45) Date of Patent: Mar. 29, 2022

(54) GUIDE APPARATUS FOR DELIVERY OF A FLEXIBLE INSTRUMENT AND METHODS OF USE

(71) Applicant: INTUITIVE SURGICAL OPERATIONS, INC., Sunnyvale, CA (US)

(72) Inventors: Carolyn M. Fenech, San Jose, CA (US); Eleadin Castaneda, San Jose, CA (US); Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 629 days.

(21) Appl. No.: 16/242,577

(22) Filed: Jan. 8, 2019

(65) Prior Publication Data

US 2019/0133702 A1    May 9, 2019

Related U.S. Application Data

(62) Division of application No. 14/276,153, filed on May 13, 2014, now Pat. No. 10,206,747.

(Continued)

(51) Int. Cl.
*A61B 5/00*     (2006.01)
*A61B 34/30*    (2016.01)
(Continued)

(52) U.S. Cl.
CPC .............. *A61B 34/30* (2016.02); *A61B 34/71* (2016.02); *A61B 2017/00477* (2013.01); *A61B 2034/301* (2016.02)

(58) Field of Classification Search
CPC ... A61B 34/30; A61B 34/71; A61B 2034/301; A61B 2017/00477
(Continued)

(56) References Cited

U.S. PATENT DOCUMENTS

| 3,382,872 A | * | 5/1968 | Rubin | ................. A61M 25/065 |
|---|---|---|---|---|
| | | | | 604/161 |
| RE31,855 E | * | 3/1985 | Osborne | ........... A61M 25/0668 |
| | | | | 604/161 |

(Continued)

FOREIGN PATENT DOCUMENTS

WO    WO-2012037506 A2    3/2012

OTHER PUBLICATIONS

Vertut, Jean and Phillipe Coiffet, Robot Technology: Teleoperation and Robotics Evolution and Development, English translation, Prentice-Hall, Inc., Inglewood Cliffs, Nj, USA 1986, vol. 3A, 332 pages.

*Primary Examiner* — May A Abouelela
(74) *Attorney, Agent, or Firm* — Haynes and Boone, LLP

(57) ABSTRACT

A guiding apparatus comprises a support assembly extending along a longitudinal axis and including a first plurality of linkages and a second plurality of linkages. The first plurality of linkages includes a first channel formation and the second plurality of linkages includes a second channel formation. The support assembly has a coupled configuration with a proximal end and a distal end in which the first plurality of linkages is coupled to the second plurality of linkages with the first and second channel formations arranged to form a continuous channel through the support assembly. The continuous channel has an opening sized to receive an elongated flexible instrument.

20 Claims, 13 Drawing Sheets

Related U.S. Application Data

(60) Provisional application No. 61/823,666, filed on May 15, 2013.

(51) Int. Cl.
 *A61B 34/00* (2016.01)
 *A61B 17/00* (2006.01)

(58) Field of Classification Search
 USPC .......................................... 600/585; 606/130
 See application file for complete search history.

(56) References Cited

U.S. PATENT DOCUMENTS

| | | | |
|---|---|---|---|
| 4,581,025 A * | 4/1986 | Timmermans | A61M 25/0668 604/264 |
| 4,687,470 A * | 8/1987 | Okada | A61M 25/02 128/DIG. 26 |
| 4,983,168 A * | 1/1991 | Moorehead | A61M 25/0668 604/161 |
| 5,158,545 A * | 10/1992 | Trudell | A61F 2/90 604/104 |
| 5,222,970 A * | 6/1993 | Reeves | A61B 17/12109 604/164.05 |
| 5,441,504 A * | 8/1995 | Pohndorf | A61M 25/0668 604/164.05 |
| 5,613,953 A * | 3/1997 | Pohndorf | A61M 25/0668 604/160 |
| 5,735,819 A * | 4/1998 | Elliott | A61M 25/04 604/160 |
| 5,902,331 A * | 5/1999 | Bonner | A61N 1/056 607/122 |
| 6,331,181 B1 | 12/2001 | Tierney et al. | |
| 6,331,732 B1 | 12/2001 | Gupta et al. | |
| 6,380,732 B1 | 4/2002 | Gilboa et al. | |
| 6,389,187 B1 | 5/2002 | Greenaway et al. | |
| 6,491,701 B2 | 12/2002 | Tierney et al. | |
| 6,758,854 B1 * | 7/2004 | Butler | A61M 25/0041 604/101.01 |
| 6,902,560 B1 * | 6/2005 | Morley | A61B 17/062 606/1 |
| 7,076,285 B2 * | 7/2006 | Windheuser | A61M 25/0097 600/434 |
| 7,314,481 B2 * | 1/2008 | Karpiel | A61F 2/95 623/1.12 |
| 7,323,006 B2 * | 1/2008 | Andreas | A61F 2/958 600/585 |
| 7,328,071 B1 * | 2/2008 | Stehr | A61N 1/0587 600/585 |
| 7,803,142 B2 * | 9/2010 | Longson | A61M 25/065 604/272 |
| 7,922,687 B2 * | 4/2011 | Gingles | A61M 31/00 604/43 |
| 7,930,065 B2 | 4/2011 | Larkin et al. | |
| 8,644,988 B2 * | 2/2014 | Prisco | A61B 34/71 700/245 |
| 9,610,129 B2 * | 4/2017 | Dejima | A61B 17/00234 |
| 2005/0234369 A1 * | 10/2005 | Voorhees | A61M 25/09041 600/585 |
| 2006/0013523 A1 | 1/2006 | Childers et al. | |
| 2007/0065077 A1 | 3/2007 | Childers et al. | |
| 2007/0156019 A1 * | 7/2007 | Larkin | B25J 19/025 600/104 |
| 2012/0289777 A1 | 11/2012 | Chopra et al. | |
| 2014/0343568 A1 | 11/2014 | Fenech et al. | |

\* cited by examiner

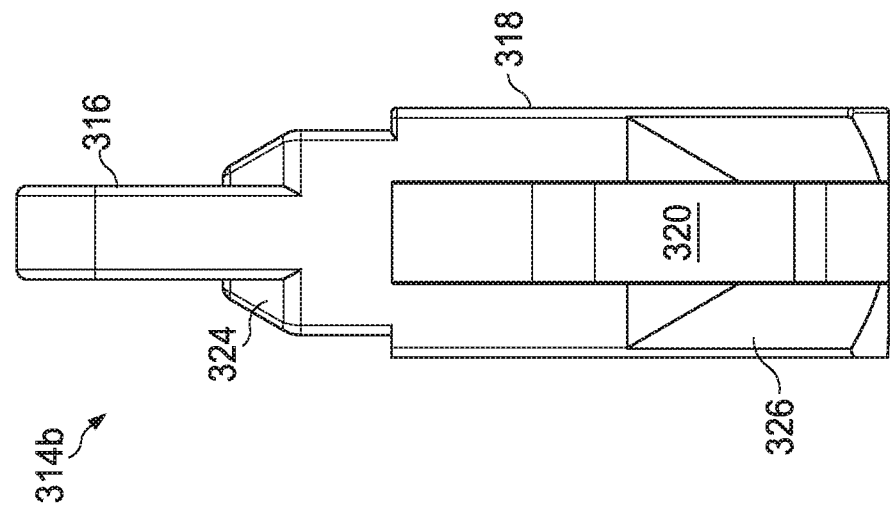
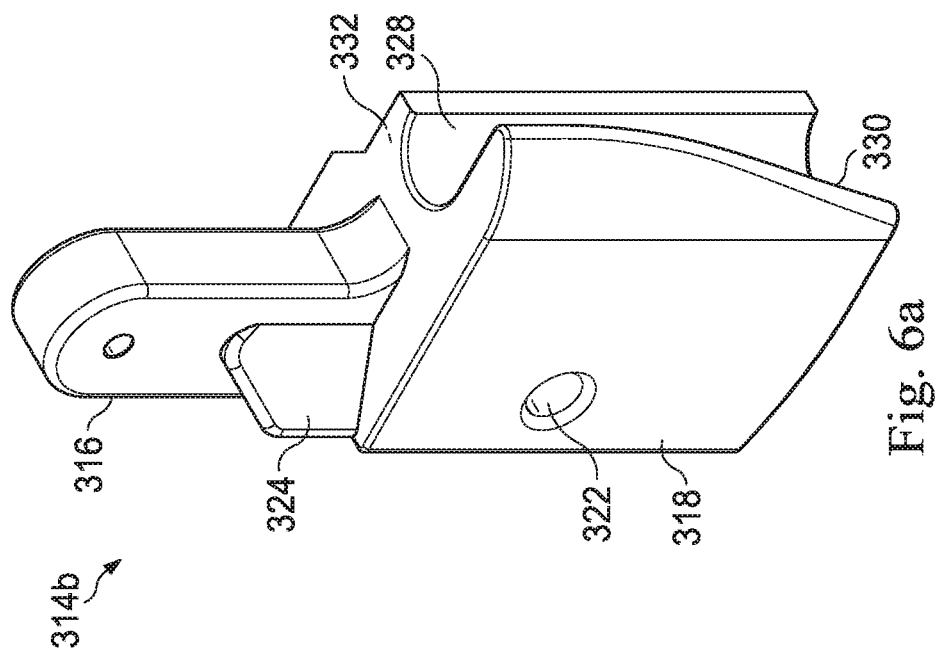

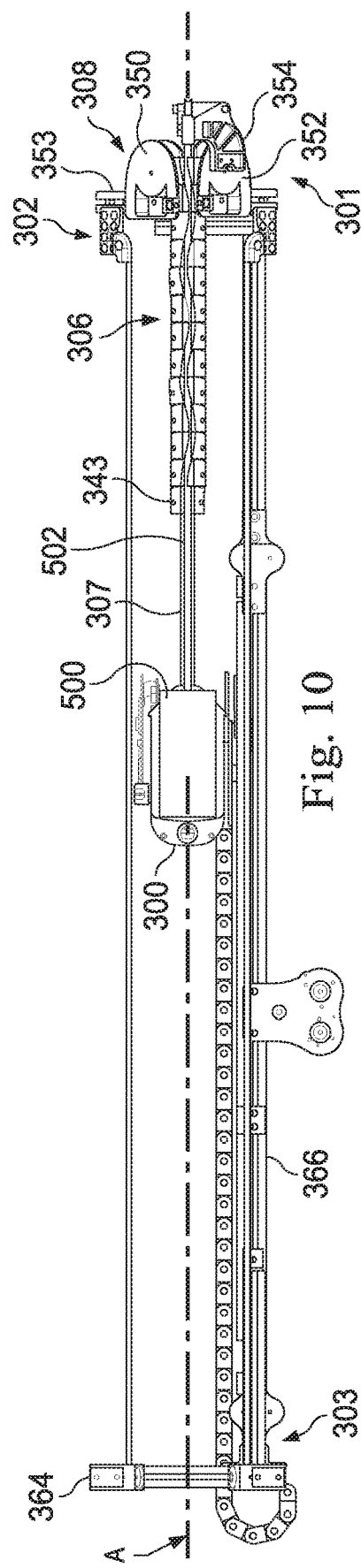

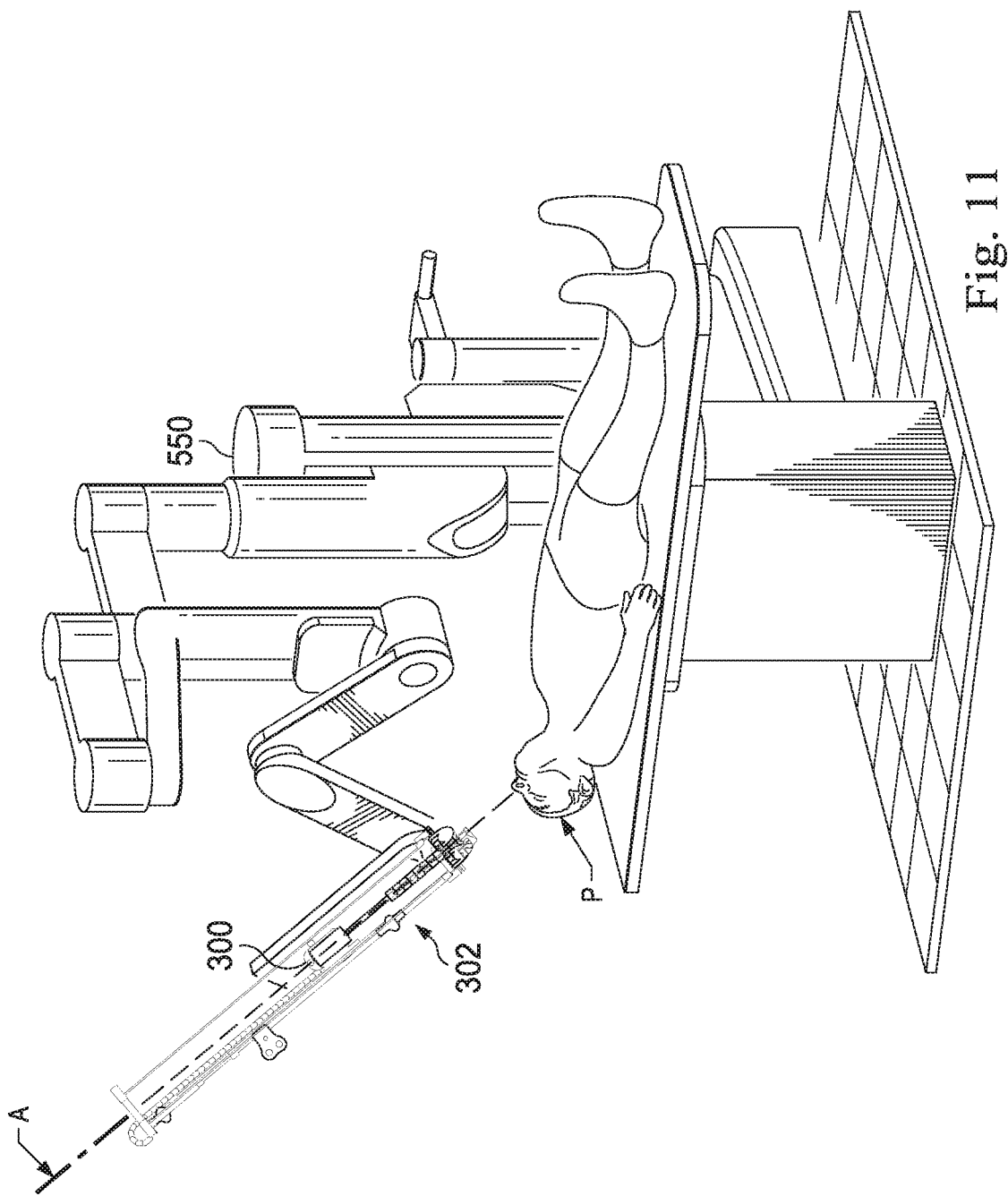

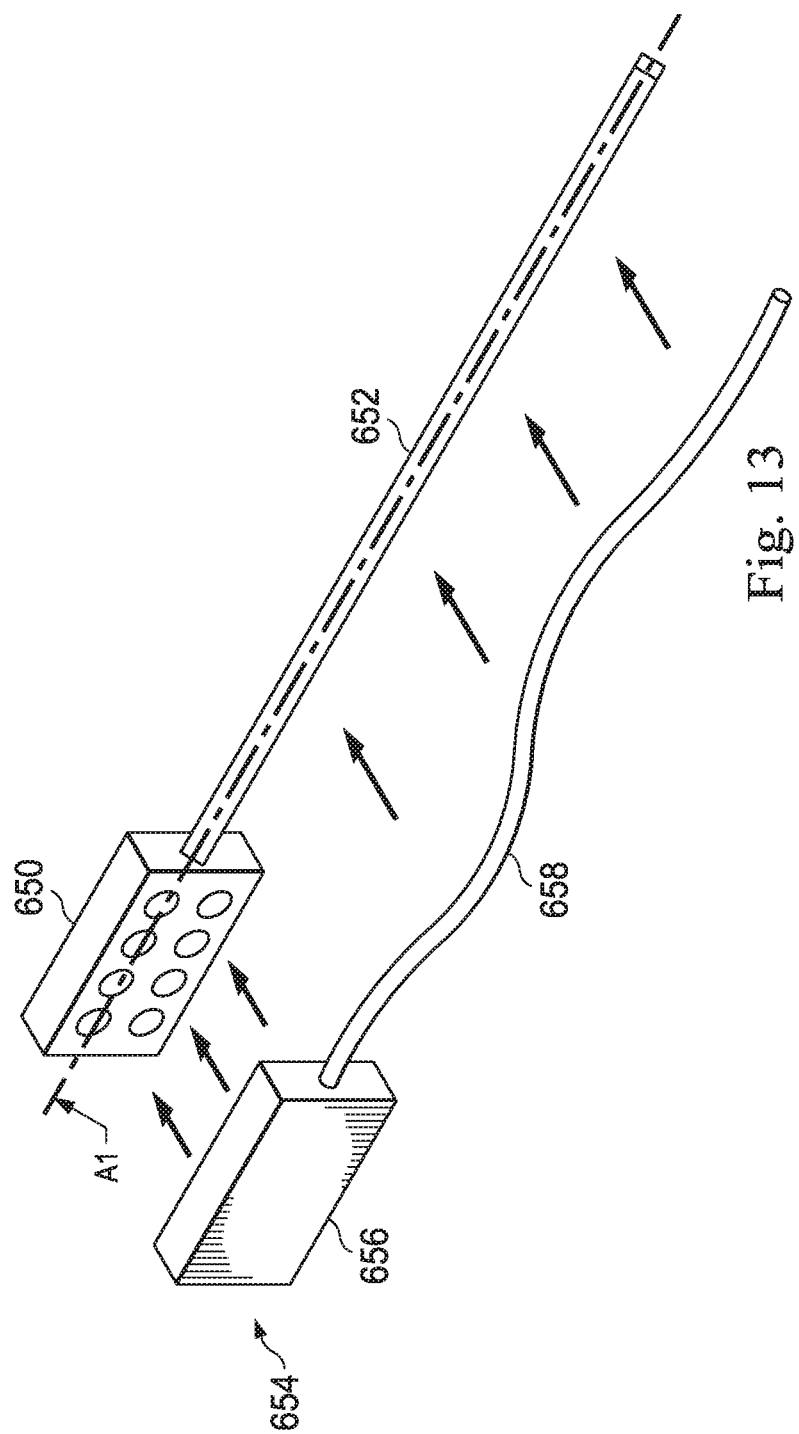

GUIDE APPARATUS FOR DELIVERY OF A FLEXIBLE INSTRUMENT AND METHODS OF USE

CROSS-REFERENCE TO RELATED APPLICATIONS

This application is a divisional of U.S. patent application Ser. No. 14/276,153, filed May 13, 2014, which claims the benefit of U.S. Provisional Application 61/823,666 filed May 15, 2013, entitled "GUIDE APPARATUS FOR DELIVERY OF A FLEXIBLE INSTRUMENT AND METHODS OF USE." The contents of each of the above-listed applications are incorporated by reference herein in their entirety.

FIELD

The present disclosure is directed to systems and methods for navigating a patient anatomy to conduct a minimally invasive procedure, and more particularly to apparatus and methods for guiding and supporting delivery of a flexible interventional instrument into a patient anatomy.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Robotic interventional systems may be used to insert the interventional instruments into the patient anatomy. In existing systems, the length of the interventional instrument extending between the patient and a robotic manipulator is unsupported which may cause the instrument to bend and buckle as it is inserted into the patient anatomy. Deformation of the instrument may damage internal components such as optical fiber shape sensors or endoscopic equipment. Improved systems and methods are needed for guiding and supporting interventional instruments as they are inserted into a patient anatomy to prevent instrument deformation.

SUMMARY

The embodiments of the invention are summarized by the claims that follow the description.

In one embodiment, an apparatus for guiding a flexible instrument comprises an elongated support assembly having a longitudinal axis. The elongated support assembly is adapted to laterally receive into engagement and longitudinally support an elongated flexible instrument.

In another embodiment, a guiding apparatus comprises an elongated support assembly extending along a longitudinal axis and having a proximal end and a distal end. The elongated support assembly includes a first support member including a channel formation and a second support member including a channel formation. The second support member is coupled to the first support member along the longitudinal axis with the channel formations of the first and second support members joined to form a continuous open channel through the support assembly. Advancement of the proximal end of the support assembly along the longitudinal axis separates the distal end of the support assembly, directing separated distal ends of the first and second support members away from the longitudinal axis.

In another embodiment, a guiding apparatus comprises a support assembly including a first plurality of linkages and a second plurality of linkages, each of the linkages of the first and second pluralities of linkages includes a channel formation. The support assembly has a coupled configuration with a proximal end and a distal end in which the first plurality of linkages is coupled to the second plurality of linkages with the channel formations arranged to form a continuous channel through the support assembly.

In another embodiment, a method of guiding an interventional instrument comprises providing an elongated support assembly extending along a longitudinal axis and having a proximal end and a distal end. The support assembly includes a first support member including a channel formation and a second support member including a channel formation. The second support member is coupled to the first support member along the longitudinal axis with the channel formations of the first and second support members joined to form a continuous channel through the support assembly. The method further comprises receiving a portion of the interventional instrument through an elongated opening of the continuous channel and moving the interventional instrument in a first direction along the longitudinal axis. The method further comprises separating a portion of the first support member from a portion of the second support member and directing the separated portions of the first and second support members away from the longitudinal axis.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 6a illustrates an oblique view of a linkage element according to an embodiment of the present invention.

FIG. 6b illustrates a side view of the linkage element of FIG. 6a.

FIG. 10 is a side view of an interventional instrument coupled to a robotic assembly and an instrument guiding apparatus according to an embodiment of the present invention.

FIG. 11 illustrates the interventional instrument and instrument guiding apparatus of FIG. 10 coupled to a robotic assembly in a patient environment according to an embodiment of the present invention.

FIG. 13 illustrates a robotic assembly and an instrument guiding apparatus according to another embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
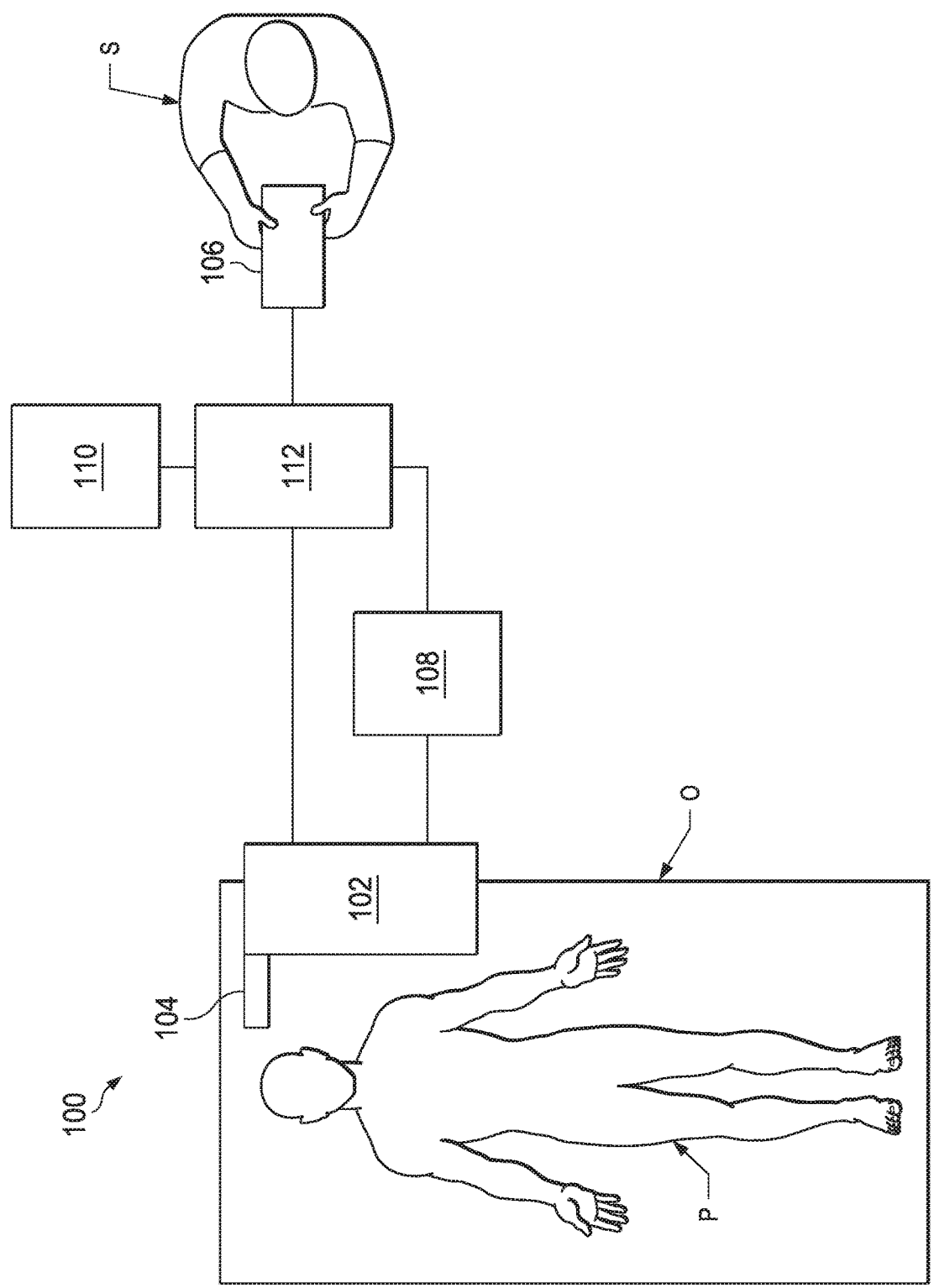
FIG. 1 is a robotic interventional system, in accordance with an embodiment of the present disclosure.

Referring to FIG. 1 of the drawings, a robotic interventional system for use in, for example, surgical, diagnostic, therapeutic, or biopsy procedures, is generally indicated by the reference numeral 100. As shown in FIG. 1, the robotic interventional system 100 generally includes a robotic assembly 102 mounted to or near an operating table O on which a patient P is positioned. An interventional instrument system 104 is operably coupled to the robotic assembly 102. An operator input system 106 allows a surgeon S to view the surgical site and to control the operation of the interventional instrument system 104.

The operator input system 106 may be located at a surgeon's console which is usually located in the same room as operating table O. However, it should be understood that the surgeon S can be located in a different room or a completely different building from the patient P. Operator input system 106 generally includes one or more control device(s) for controlling the interventional instrument system 104. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 102 supports the interventional instrument system 104 and may comprise a kinematic structure of one or more non-servo controlled links (e.g., one or more links that may be manually positioned and locked in place, generally referred to as a set-up structure) and a robotic manipulator. The robotic assembly 102 includes plurality of actuators (e.g., motors) that drive inputs on the interventional instrument 104. These motors actively move in response to commands from the control system (e.g., control system 112). The motors include drive systems which when coupled to the interventional instrument 104 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 100 also includes a sensor system 108 with one or more sub-systems for receiving information about the instruments of the robotic assembly. Such sub-systems may include a position sensor system (e.g., an electromagnetic (EM) sensor system); a shape sensor system for determining the position, orientation, speed, pose, and/or shape of the catheter tip and/or of one or more segments along a flexible body of instrument 104; and/or a visualization system for capturing images from the distal end of the catheter system.

The robotic interventional system 100 also includes a display system 110 for displaying an image of the surgical site and interventional instruments 104 generated by sub-systems of the sensor system 108. The display 110 and the operator input system 106 may be oriented so the operator can control the interventional instrument system 104 and the operator input system 106 as if viewing the workspace in substantially true presence. True presence means that the displayed tissue image appears to an operator as if the operator was physically present at the image location and directly viewing the tissue from the perspective of the image.

Alternatively or additionally, display system 110 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images and models.

In some embodiments, the display system 110 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 110 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 104 may be superimposed on the virtual image to assist the surgeon controlling the interventional instrument.

The robotic interventional system 100 also includes a control system 112. The control system 112 includes at least one processor (not shown), and typically a plurality of processors, for effecting control between the interventional instrument system 104, the operator input system 106, the sensor system 108, and the display system 110. The control system 112 also includes programmed instructions (e.g., a computer-readable medium storing the instructions) to implement some or all of the methods described herein. While control system 112 is shown as a single block in the simplified schematic of FIG. 1, the system may comprise a number of data processing circuits with a portion of the processing optionally being performed on or adjacent the robotic assembly 102, a portion being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers to provide force and torque feedback from the interventional instrument system 104 to one or more corresponding servomotors for the operator input system 106. The servo controller(s) may also transmit signals instructing robotic assembly 102 to move the interventional instruments 104 which extend into an internal surgical site within the patient body via openings in the body. Any suitable conventional or specialized servo controller may be used. A servo controller may be separate from, or integrated with, robotic assembly 102. In some embodiments, the servo controller and robotic assembly are provided as part of a robotic arm cart positioned adjacent to the patient's body.

The control system 112 may further include a virtual visualization system to provide navigation assistance to the interventional instruments 104. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 100 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
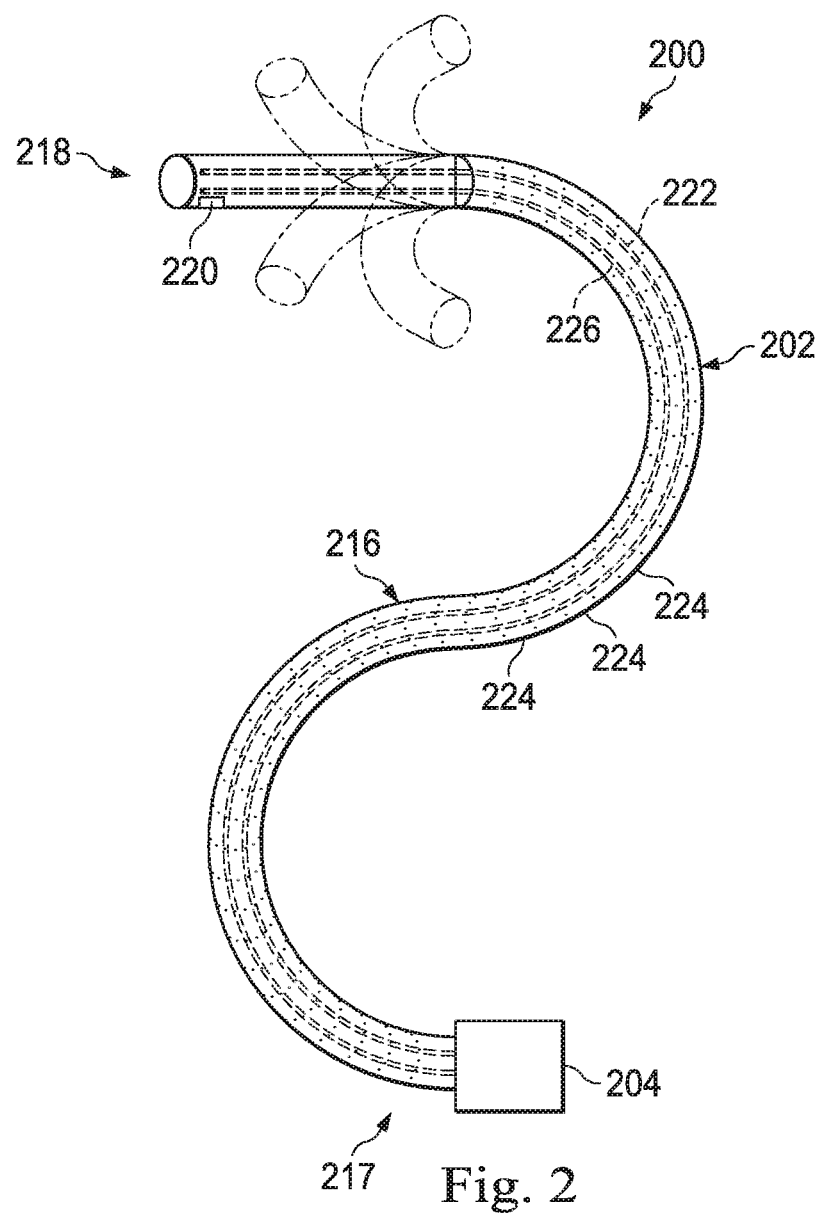
FIG. 2 illustrates an interventional instrument system utilizing aspects of the present disclosure.

FIG. 2 illustrates an interventional instrument system 200 which may be used as the interventional instrument system 104 of robotic interventional system 100. Alternatively, the interventional instrument system 200 may be used for non-robotic exploratory procedures or in procedures involving traditional manually operated interventional instruments, such as endoscopy.

The instrument system 200 includes a catheter system 202 coupled to an instrument body 204. The catheter system 202 includes an elongated flexible catheter body 216 having a proximal end 217 and a distal end 218. In one embodiment, the flexible body 216 has an approximately 3 mm outer diameter. Other flexible body outer diameters may be larger or smaller. The catheter system 202 may optionally include a shape sensor 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. If the instrument system 200 is an interventional instrument system 104 of a robotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed to detect the shape of the catheter system 202 and for utilizing that information to assist in surgical procedures. The sensor system (e.g. sensor system 108 or another type of tracking system as described in FIG. 3) may include an interrogation system for generating and detecting the light used for determining the shape of the catheter system 202. This information, in turn, in can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The interventional instrument system may optionally include a position sensor system 220 (e.g., an electromagnetic (EM) sensor system) which may be disabled by an operator or an automated system (e.g., a function of the control system 112) if it becomes unreliable due to, for example, magnetic interference from other equipment in the surgical suite or if other navigation tracking systems are more reliable.

The position sensor system 220 may be an EM sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 includes a channel sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like. In various embodiments, the auxiliary tool 226 may be an image capture probe including a tip portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The flexible catheter body 216 may also house cables, linkages, or other steering controls (not shown) that extend between the instrument body 204 and the distal end 218 to controllably bend or turn the distal end 218 as shown for example by the dotted line versions of the distal end. In embodiments in which the instrument system 200 is actuated by a robotic assembly, the instrument body 204 may include drive inputs that couple to motorized drive elements of the robotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. Also or alternatively, the flexible body 216 can define one or more lumens through which interventional instruments can be deployed and used at a target surgical location.

In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

When using a robotic assembly to insert an instrument catheter into a patient anatomy, the outstretched catheter should be supported as the catheter is advanced into the patient. Otherwise, as the catheter is pushed from a proximal end and encounters friction in the patient anatomy at the distal end, the catheter may buckle or bend. To prevent this deformation of the catheter, an instrument guiding apparatus, as described herein, may be used to provide rigid support to the catheter until it enters the patient anatomy. As the catheter enters the patient anatomy, the guiding apparatus peels away from the catheter and moves to an unobtrusive location. Thus, the maximum length of the catheter may be used for patient treatment.

Figure 3:
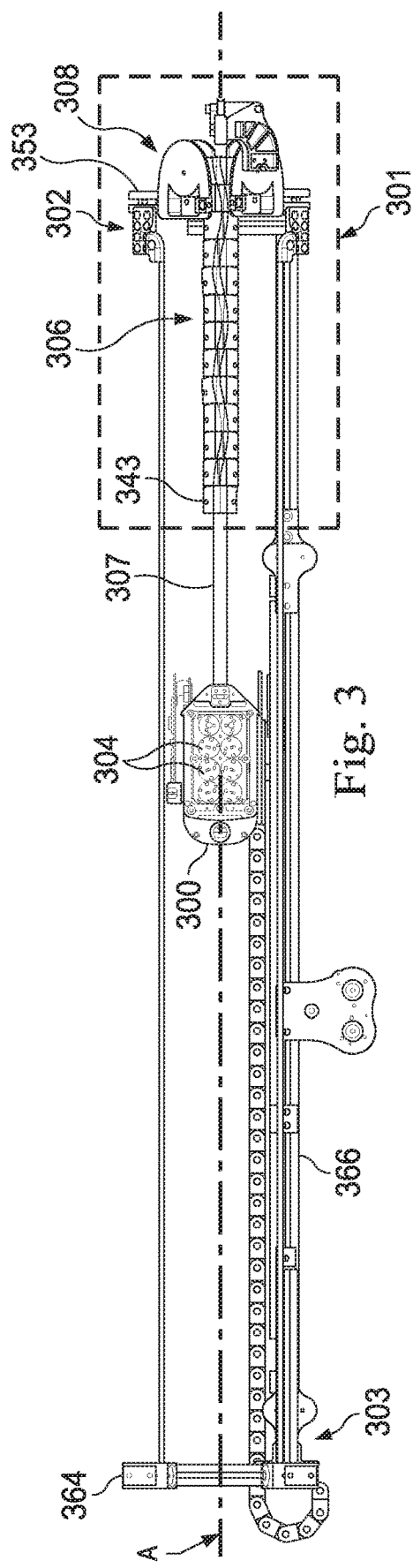
FIG. 3 is a side view of a robotic assembly and an instrument guiding apparatus according to an embodiment of the present invention.

FIG. 3 illustrates an instrument interface portion 300 of a robotic assembly (e.g. robotic assembly 102) and an instrument guiding apparatus 302 according to an embodiment of the present invention. The instrument interface portion 300 incudes drive inputs 304 to provide mechanical coupling of the instrument end effector and flexible body steering mechanism to the drive motors mounted to the robotic manipulator. For example, a pair of drive inputs may control the pitch motion of the distal end of the instrument flexible body, with one adaptor of the pair controlling motion in the upward direction and the other of the pair controlling motion in the opposite downward direction. Other pairs of drive inputs may provide opposing motion in other degrees of freedom for the flexible body and/or the end effector. Instrument interfacing with robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The instrument interface portion 300 may also control instrument insertion by moving linearly along an insertion axis A.

Figure 4:
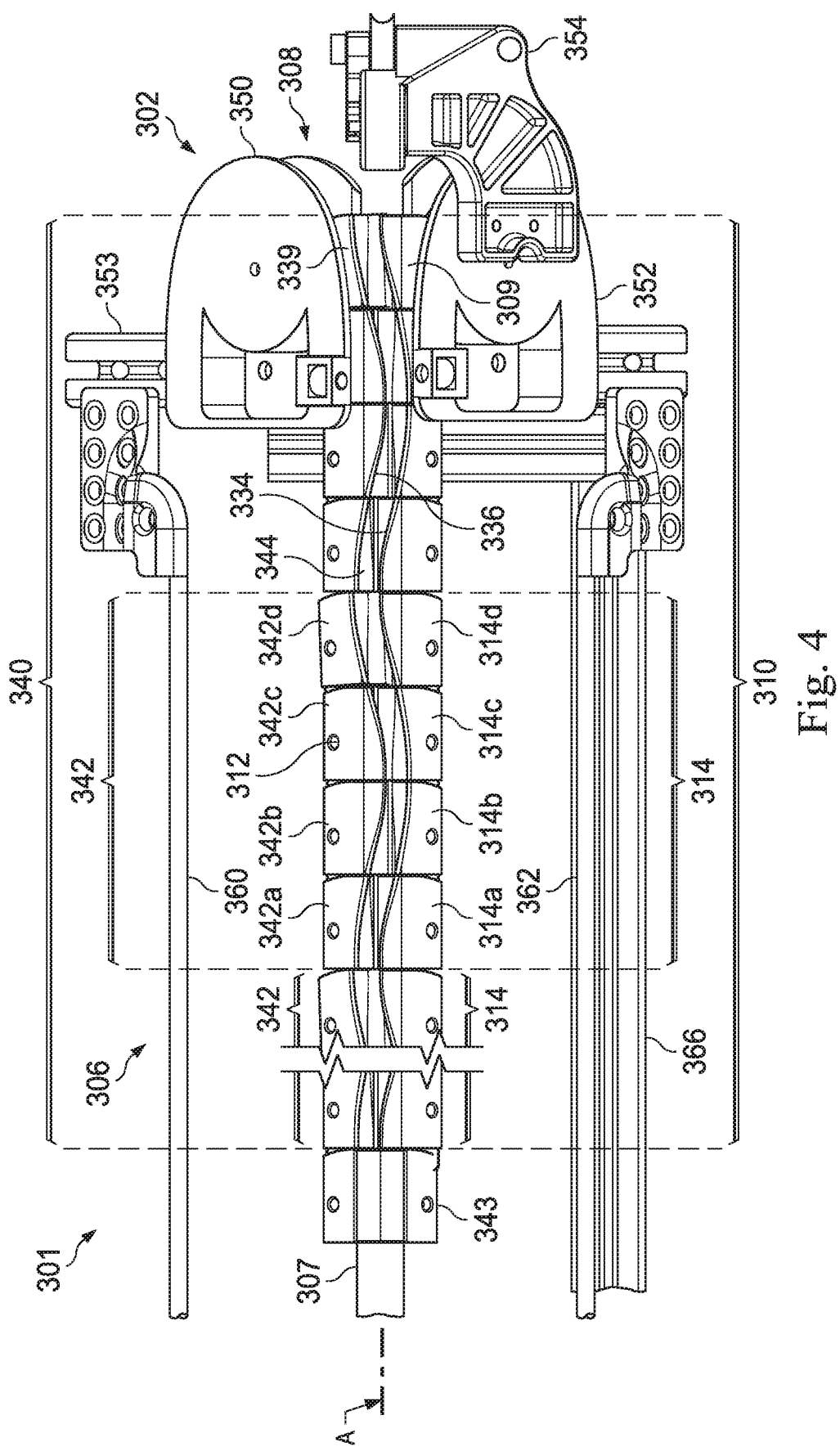
FIG. 4 illustrates the distal end of the instrument guiding apparatus of FIG. 3 in an initial configuration.

The instrument guiding apparatus 302 has a distal end 301 and a proximal end 303. The instrument guiding apparatus 302 includes an elongated support assembly 306 and a mounting strut 307 for coupling the instrument interface portion 300 to the assembly 306. The instrument guiding apparatus 302 further includes a return assembly 308. The distal end 301 of the instrument guiding apparatus 302 is shown in detail in FIG. 4 in an initial configuration. The elongated support assembly 306 includes lower support component 309 with linkages 310 connected in series by hinge components 312. In this embodiment, the linkages 310 are arranged in subsets of linkages 314 that form a repeating pattern of linkages 314a, 314b, 314c, 314d.

As an example, linkage 314a is illustrated in detail in FIGS. 6a and 6b. The linkage 314a includes a projection 316 and a body portion 318. The body portion 318 includes a recessed portion 320 sized and shaped to receive the projection 316 of a serially connected adjacent linkage (e.g. linkage 314b). A pin (not shown) extends through an aperture 322 in body portion 318 to couple projection 316 of the adjacent linkage, thus hingedly coupling the adjacent linkages. An optional wedge component 324 is sized and shaped to extend into a recess 326 of the adjacent linkage to provide additional longitudinal stability to the lower support component 309. The body portion 318 includes a channel formation 328, a curved edge portion 330, and an interlocking surface 332. The interlocking surface 332 may be a generally planar abutment surface and/or may include keyed features for interconnection with mating features of a paired linkage. The linkages 310 may be formed of any of a variety of rigid or semi-rigid materials including metals, polymers, or rubber. Within each subset 314, each linkage has a different channel formation and curved edge portion such that when serially assembled, the curved edge portions form a continuous undulated edge 334.

Referring again to FIG. 4, the elongated support assembly 306 also includes an upper support component 339 having linkages 340 also hingedly connected in series. The terms "upper support component" and "lower support component" are used only to distinguish the support components and are not limiting in any way. The linkages 340 are arranged in subsets of linkages 342 that form a repeating pattern of linkages 342a, 342b, 342c, 342d. The interlocking surfaces of the linkages 342 are paired with and interlocked to linkages 314 (e.g., linkage pair 314a, 342a; linkage pair 314b, 342b, etc.) such that the channel formations of each of the linkages are linearly aligned generally along the insertion axis A to form a continuous channel formation 344 through the elongated support assembly 306. The continuous undulated edge 334 of the linkages 314 is spaced apart from a continuous undulated edge 336 of linkages 342. The gap between the undulated edges 334, 336 forms an elongated undulating or serpentine opening to the continuous channel formation 344. The proximal-most linkages 314a, 342a in each support component are coupled to a mounting link 343. The mounting link 343 is coupled to the mounting strut 307.

In various alternative embodiments, the subsets of linkages 314 may have fewer or more than four linkages to create a section of a repeating undulating edge pattern. In other alternative embodiments, the adjacent linkages in each support component may be coupled by other types of joints such as living hinge continuous flexures. In still other alternative embodiments, the elongated support components may be continuously formed providing longitudinal structural stability when aligned along the axis A, but having sufficient flexibility to move around the return assembly 308. For example, a continuous length of semi-rigid material or a notched rigid material may be used. In still other alternative embodiments, a support assembly may be split into multiple support components, rather than just two. In still other alternative embodiments, the length of the support components (and thus the number of repeating linkage subsets) may be longer or shorter to support catheters of different sizes. In still other alternative embodiments, the diameter of the channel formation 344 may be sized to accommodate different diameter catheters. In still other alternative embodiments, the diameter of the channel formation 344 may vary along its length to match the diameter of a catheter with a diameter varying along its length.

Figure 5:
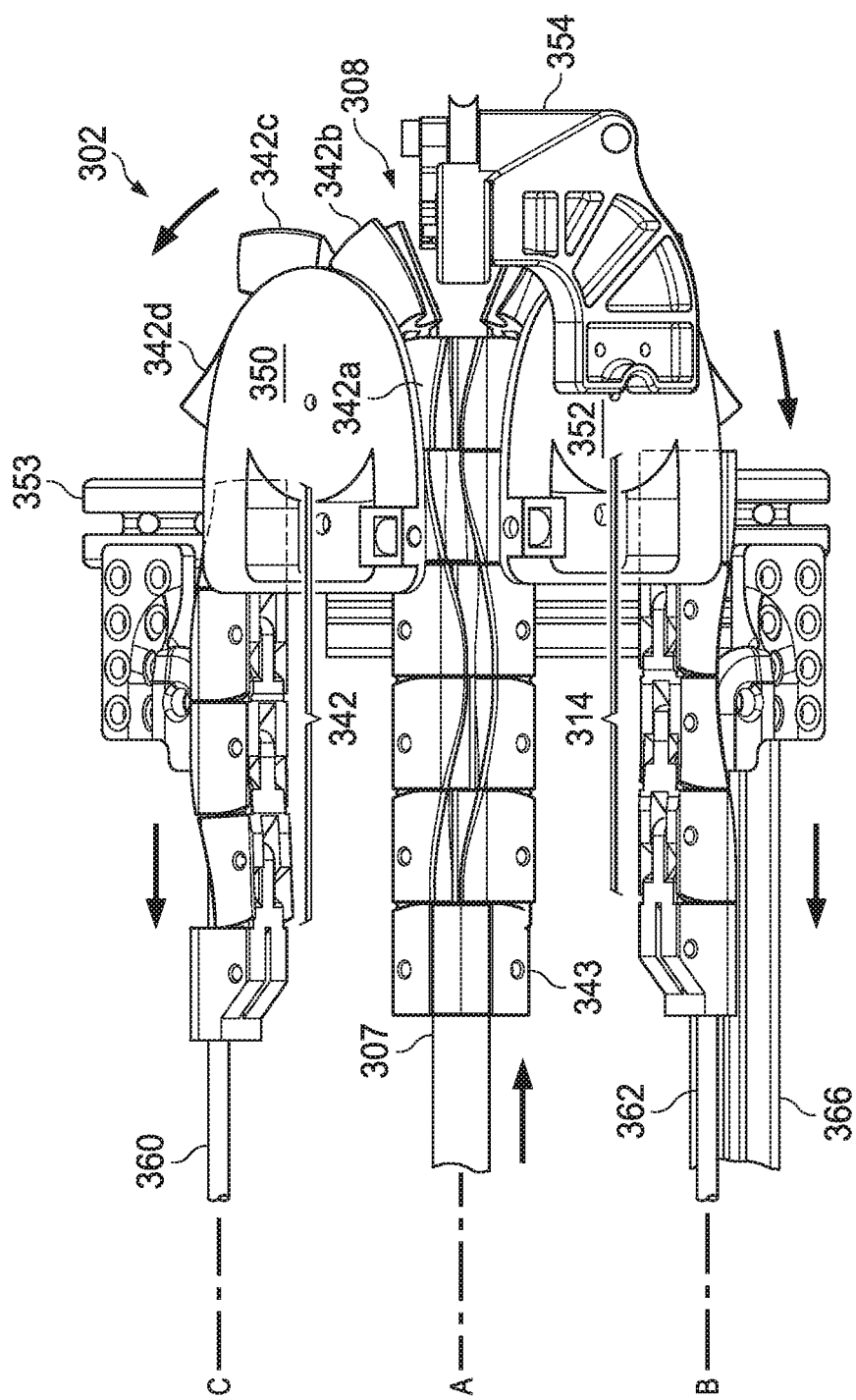
FIG. 5 illustrates the distal end of the instrument guiding apparatus of FIG. 3 in an operating configuration.

In operation, as shown in FIG. 5, movement of the instrument interface portion 300 distally along the axis A advances the mounting strut 307 which moves the proximal end of the elongated support assembly 306 distally. As the proximal end of the elongated support assembly 306 is moved distally, the linkages 340 are separated from the linkages 310. The separated linkages 340, 310 are directed to the return assembly 308.

Figure 7:
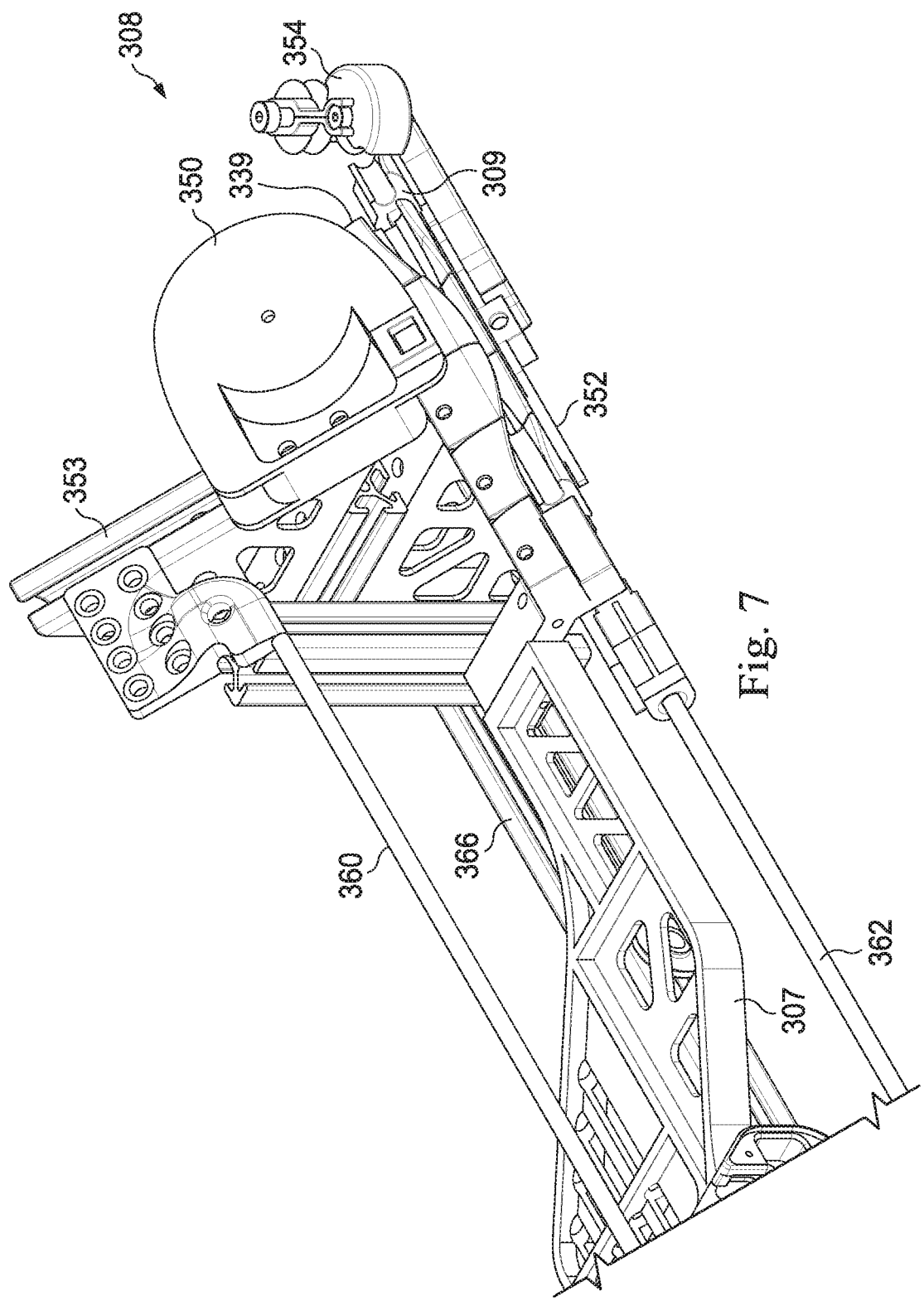
FIG. 7 illustrates the distal end of the instrument guiding apparatus of FIG. 3 and a mounting strut coupling the guiding apparatus to the robotic assembly.
Figure 8:
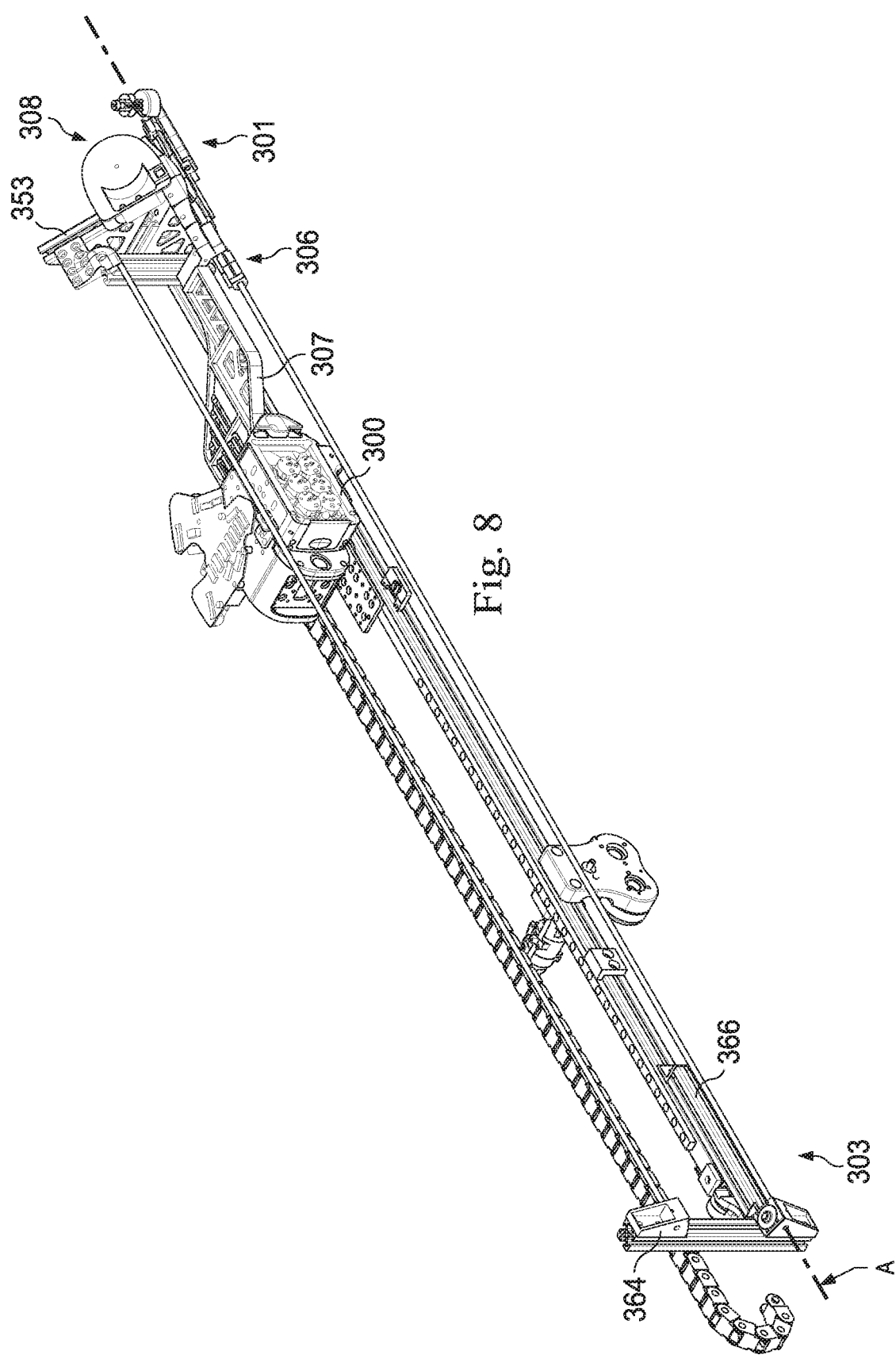
FIG. 8 is an oblique view of the robotic assembly and the instrument guiding apparatus of FIG. 3.

The return assembly 308 includes a return guide 350 and a return guide 352. In this embodiment, the return guides 350 and 352 are arranged at an approximately 90° angle to each other about the axis A (as seen more clearly in FIGS. 7 and 8). The return guides 350, 352 are attached to a bracket 353. The linkages 310 wrap around the return guide 352 and the linkages 340 wrap around the return guide 350, directing the linkages away from the axis A. As the proximal end of the elongated support assembly 306 is advanced further distally, linkages 310 move approximately 180° around the return guide 352 and the leading linkages of the linkages 310 begin moving proximally (in a direction generally opposite the linear motion of the instrument interface portion 300) along an axis B, aligned generally parallel to the axis A. Similarly, as the linkages 340 move approximately 180° around the return guide 350 and the leading linkages of the linkages 340 move proximally (in a direction generally opposite the linear motion of the instrument interface portion 300) along an axis C, aligned generally parallel to the axis A. In alternative embodiments, the linkages may return at an angle greater or less than 180°.

Figure 9B:
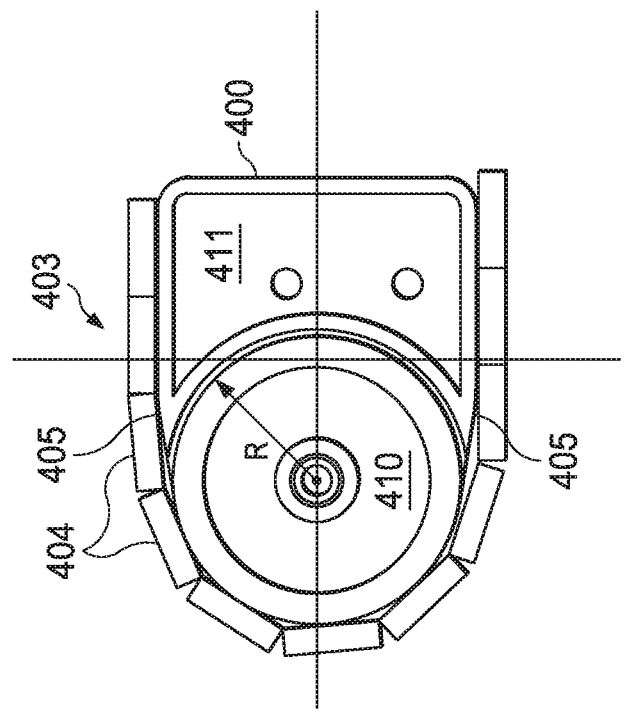
FIGS. 9a and 9b illustrate the effect of linkage size on chordal action around a return assembly.
Figure 9A:
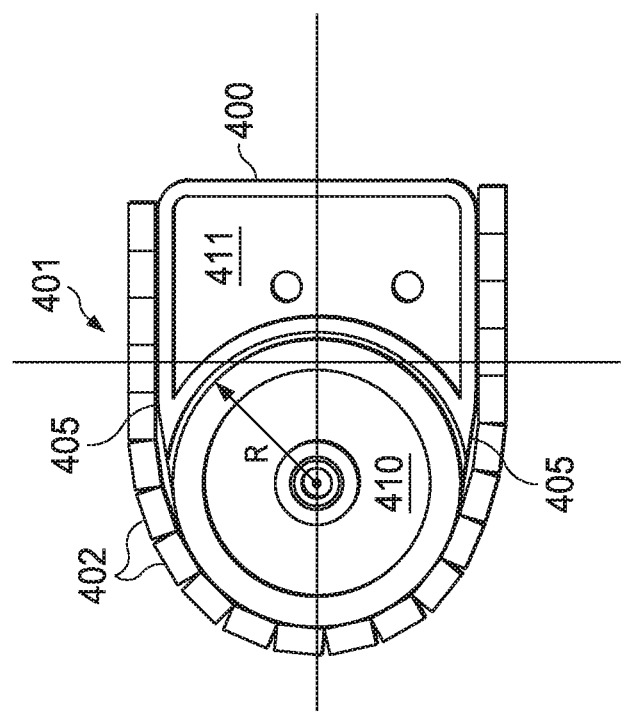

The return guides 350, 352 may have a circular or elliptical shape sized to minimize the chordal effect between the linkages and the guides. In other words, to maintain a relatively consistent velocity of the linkages around the guides while minimizing any lurching or pulsating motion of the linkages, the return guide shape is selected in view of the size of the linkages. As shown in FIGS. 9a and 9b, a return guide 400 includes circular component 410 having a radius R. The circular component may be rotatable or may be stationary. A rotatable circular component may be powered or passively rotatable. The return guide 400 also includes a delivery component 411 that includes entrance and exit ramps 405 that direct the linkages onto the return guide. The entrance and exit ramps are sized and shaped to direct the linkages at a constant height and constant speed onto the return guides. The circular component 410 may rotate relative to the delivery component 411. In various alternative embodiments, the circular component and the delivery component may be a unitary structure with a noncircular curvature surface that integrates the entrance and exit ramps with an arc of the circular component. In other embodiments, the unitary structure with a noncircular curvature may have an elliptical or parabolic curve.

As shown in FIG. 9a, a linkage assembly 401 has linkages 402. As shown in FIG. 9b, a linkage assembly 403 has linkages 404. Generally, the larger the linkages are, the greater the chordal effect that will be experienced, if the size of the return guide is held constant. Likewise, a larger radius return guide exhibits less chordal effect than a smaller circle, if the size of the linkages is held constant. Smaller linkages, while often preferable to minimize chordal effect, may result in a less rigid construction when the linkage assembly is aligned along the insertion axis A. Thus, the design of the linkage assembly and the size of the linkages must take into consideration the (often opposing) factors of chordal effect and linkage assembly rigidity. The size of the return guides also affects the length of the proximal end of the catheter that is retained in the instrument guiding apparatus 302 and thus is unusable for patient treatment. For example, the larger the radius R of the return guide, the greater the length of unusable catheter.

Optionally, to facilitate the movement of the linkages around the return guides, one or more push or pull systems may be utilized. For example, the return guides may include a freely-rotating wheel which rotates with the linkages as the proximal end of the elongated support assembly is moved distally. In various alternative embodiments, the rotating wheel may include sprockets, a belt, or other friction-based device that pulls or pushes the linkages around the return guide. Alternatively or additionally, guiding wires may be attached to the leading linkages of the support members 310, 340. As the proximal end of the elongated support assembly is moved distally, the guiding wires pull the leading linkages of the support components 309, 339. The guiding wires may advance in a generally proximal direction (opposite the direction of insertion) along the axes B, C as the instrument interface portion 300 moves distally. In various embodiments, the guiding wires may be connected to the instrument interface portion such that a guiding wire, the instrument interface portion, and a support member form a moving loop.

Referring again to FIGS. 3, 5, 7, and 8 the return assembly 308 further includes a return support 360 extending generally along the axis C. The return support 360 includes a rod member sized to extend through the channel formation of the upper support component 339, supporting and maintaining the alignment of the support member as the linkages 340 move proximally along the axis C. Likewise, the return assembly 308 includes a return support 362 generally aligned along the axis B. The return support 362 includes a rod member sized to extend through the channel formation of the lower support component 309, supporting and maintaining the alignment of the support member as the linkages 310 move proximally along the axis B. The return supports 360, 362 are coupled to and maintained in generally parallel alignment by a bracket 364. The bracket 364 is rigidly coupled to a bracket 366 which extends generally parallel to the insertion axis A. The bracket 366 is rigidly coupled to the bracket 353.

Referring again to FIGS. 4 and 5, an instrument support 354 extends distally from the return guide 352 and distally of the location at which the linkages 310 separate from the linkages 340. In alternative embodiments, the instrument support 354 may be supported by the return guide 350, the bracket 353, and/or the bracket 366.

FIG. 10 illustrates an interventional instrument system 500 (e.g., the interventional instrument 200) coupled to the robotic interface portion 300. FIG. 11 illustrates the interventional instrument 500 and instrument guiding apparatus 302 coupled to robotic manipulator assembly 550 which includes the interface portion 300. The instrument 500 is positioned in a surgical environment with a patient anatomy P. As shown in FIG. 10, the instrument system 500 includes an elongated flexible catheter 502 extending generally along the insertion axis A when the instrument system is coupled to the robotic interface. To support the longitudinal length of the catheter during patient insertion, a clinician inserts catheter 502 between the undulated edges 334, 336 through the elongated undulated opening and into the channel formation 344. The catheter 502 is laterally inserted in a direction generally perpendicular to the insertion axis A. The catheter 502 is able to flex slightly to conform to the undulated opening. Inside the elongated support assembly 306, the flexible catheter 502 returns to a generally straight configuration with the channel formations 328 and curved edges 380 of the linkages retaining the catheter 502 and preventing it from migrating from the continuous channel through the undulated opening. Thus, the flexible catheter 205 is laterally received into engagement with the elongated support assembly 306. As compared to a support assembly that requires entry of the catheter into the channel formation through a proximal opening, the elongated undulated opening also may allow the catheter 502 to be more efficiently attached and detached from the interface portion 300 without the need for moving the interface portion proximally along the axis of insertion A. The elongated side-opening channel also allows a catheter that is already partially inserted into a patient to be coupled to the robotic assembly without removing the catheter.

The elongated support assembly 306 may support the catheter 502 along its complete or partial length. With the support components 309, 339 interlocked along the insertion axis A, the support assembly 306 minimizes bending or buckling of the catheter 502 as the distal end of the catheter 502 is advanced into the patient anatomy P. Any significant bending or buckling of the catheter 502 may damage optical fibers used for shape sensing or endoscopy. Also, bending or buckling may make advancing the catheter non-intuitive, since the user will observe no distal tip movement even though the user is advancing the proximal end of the catheter. In the described embodiments, the support components 309, 339 form a self-supporting structure that requires no support rails or other rigid, elongated supports along the axis A. Thus, the support components 309, 339 are able to move out of the path of the advancing robotic interface portion 300.

As the robotic interface portion 300 is advanced, under a clinician's control, distally along the insertion axis A, it also moves the catheter 502 and the proximal end of the elongated support assembly 306 distally. At the distal end 301 of the instrument guiding apparatus 302, the return assembly 308 incrementally separates the elongated support assembly 306 along the axis A into the lower support component 309 which is routed around the return guide 350 and into the upper support component 309 which is routed around the return guide 352. As the support components 309, 339 are directed away from the axis A, the catheter 502 continues to advance distally past the distal end 301 of the instrument guiding apparatus 302 for insertion into the patient anatomy P. Optionally, the instrument support 354 may support the length of the catheter 502 extending between the patient anatomy and the distal end 301 of the instrument guiding apparatus 302. As the catheter is removed from the patient, the support components 309, 339 move in reverse, reassembling into the interlocked support assembly to support the withdrawn catheter.

Figure 12:
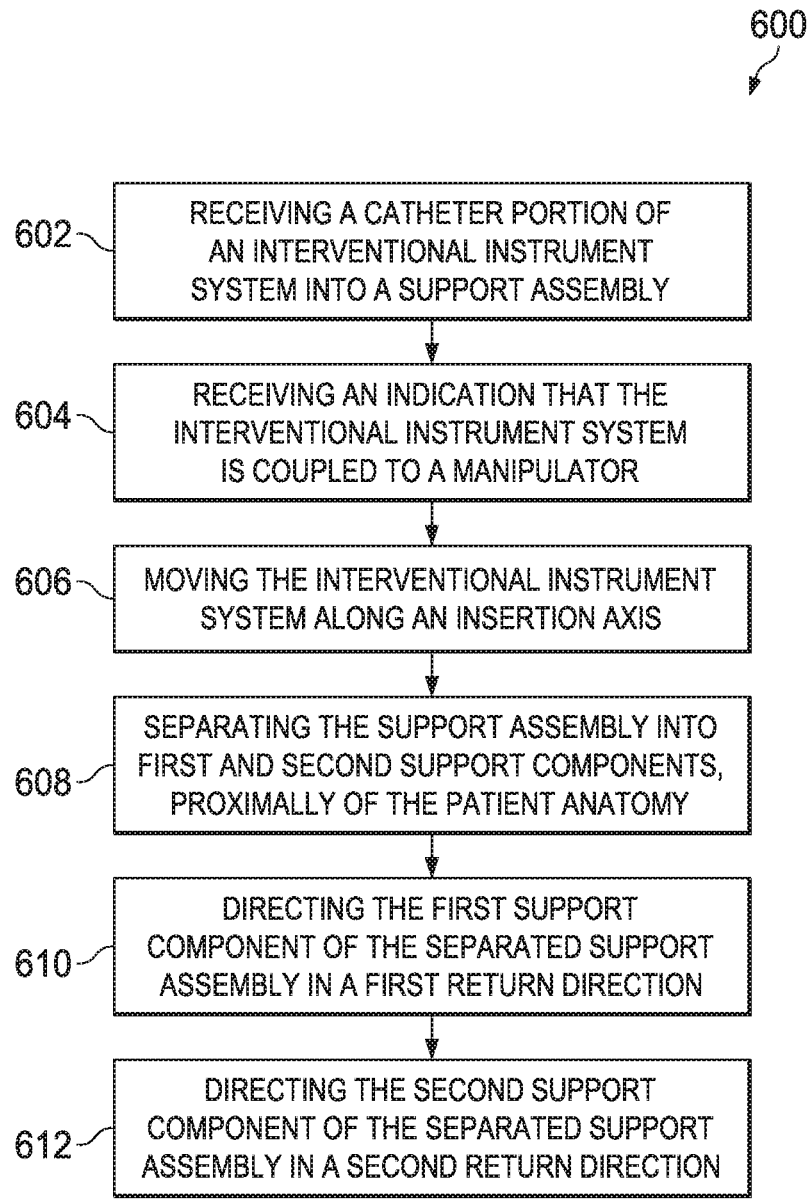
FIG. 12 is a flowchart describing a method of guiding an interventional instrument according to an embodiment of the present disclosure.

FIG. 12 provides a method 600 of guiding an interventional instrument (e.g., instrument 500) using the instrument guiding apparatus 302. At 602, the method 600 includes receiving a catheter portion of an interventional instrument system into a support assembly. As described above, the catheter portion of the interventional instrument may be inserted through an elongated undulated opening into a continuous channel formation of the support assembly. The direction of insertion may be generally perpendicular to the axis of insertion of the interventional instrument. At 604, the method 600 includes receiving an indication at the robotic control system that the interventional instrument system is coupled to the robotic manipulator. At 606, the method 600 includes advancing the interventional instrument system along the insertion axis A. At 608, the method 600 includes incrementally separating the distal end of the support assembly into separated first and second support components. As the support assembly is incrementally separated in two, the distal catheter portion of the interventional instrument is advanced distally into the patient anatomy. The proximal portion of the catheter remains supported by the interlocked support assembly. The location at which the support assembly is separated may be located as dose as is practicable to the entrance to the patient anatomy to limit the length of the catheter that is unsupported between the support assembly and the entrance to the patient anatomy. At 610, the method 600 includes directing the first support component of the separated support assembly in a first return direction, away from the insertion axis A. At 612, the method 600 includes directing the second support component of the separated support assembly in a second return direction, away from the insertion axis A. As previously described, the separated support components of the support guide may be routed to a return assembly that directs the support components in different directions away from the catheter portion and the insertion axis A.

FIG. 13 illustrates a robotic assembly 650 and an instrument guiding apparatus 652 extending along an insertion axis A1 according to another embodiment of the present disclosure. An interventional instrument system 654 (e.g., instrument system 200) includes an adaptor portion 656 and a catheter portion 658. In this embodiment, the instrument system 654 couples to the instrument guiding apparatus 652 in a lateral direction, generally perpendicular to the insertion axis A1. The adaptor portion 656 couples to the robotic assembly 650 as previously described. In this embodiment, the catheter portion 658 attaches directly to the instrument guiding apparatus 652 via, for example, magnetic force, discrete fasteners, or adhesive connection. The catheter portion 658 is longitudinally supported by the guiding apparatus 652 along its length, preventing buckling or bending of the catheter portion. When coupled, catheter portion 658 may be longitudinally fixed (along axis A1) with respect to the instrument guiding apparatus 652. As such, the longitudinal movement of the robotic assembly 650 along the insertion axis A1 moves the catheter portion 658 together with the instrument guiding apparatus 652, without substantial sliding of the catheter portion relative to the instrument guiding apparatus. In this embodiment, as the catheter portion 658 enters the patient anatomy, the instrument guiding apparatus 652 can be separated from the catheter portion 658 and routed away from the axis A1 as a single member. The lateral attachment of the catheter to the guide apparatus allows a clinician to attach a catheter portion that has already been inserted into a patient anatomy to the instrument guiding apparatus.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A guiding apparatus comprising:
   a support assembly extending along a longitudinal axis and including:
      a first plurality of linkages including a first channel formation; and
      a second plurality of linkages including a second channel formation;
   wherein the support assembly has a coupled configuration with a proximal end and a distal end in which the first plurality of linkages is coupled to the second plurality of linkages with the first and second channel formations arranged to form a continuous channel through the support assembly, wherein the continuous channel has an opening sized to receive an elongated flexible instrument.

2. The guiding apparatus of claim 1 further comprising:
   a first return assembly;
   a second return assembly; and
   a strut having a proximal portion and a distal portion, wherein the distal portion of the strut is coupled to a proximal end of the first and second plurality of linkages,
   wherein advancement of the distal portion of the strut along the longitudinal axis moves the distal end of the support assembly from the coupled configuration to a decoupled configuration in which a portion of the first plurality of linkages is separated from a portion of the second plurality of linkages.

3. The guiding apparatus of claim 2 wherein the first return assembly includes a curved surface and the second return assembly includes a curved surface, wherein the separated portion of the first plurality of linkages is configured to advance along the curved surface of the first return assembly and the separated portion of the second plurality of linkages is configured to advance along the curved surface of the second return assembly.

4. The guiding apparatus of claim 3 wherein the first return assembly further includes a return guide adapted to guide the separated portion of the first plurality of linkages in a direction approximately parallel to the longitudinal axis.

5. The guiding apparatus of claim 1 wherein adjacent linkages of the first plurality of linkages are pivotably coupled to each other by a hinge.

6. The guiding apparatus of claim 1 wherein adjacent linkages of the first plurality of linkages are coupled by a flexible material.

7. The guiding apparatus of claim 1 wherein the first channel formation of the first plurality of linkages forms a first undulated edge in the coupled configuration.

8. The guiding apparatus of claim 7 wherein the second channel formation of the second plurality of linkages forms a second undulated edge in the coupled configuration, wherein the first and second undulated edges form the opening of the continuous channel, wherein the opening is sized to receive the elongated flexible instrument in a direction generally perpendicular to the longitudinal axis.

9. The guiding apparatus of claim 1 wherein each linkage of the first plurality of linkages includes a first locking feature and each linkage of the second plurality of linkages includes a second locking feature, wherein, in the coupled configuration, each first locking feature interlocks with a corresponding one of the second locking features.

10. The guiding apparatus of claim 2 wherein the strut extends between the proximal end of the support assembly and an interface portion of a robotic manipulator.

11. The guiding apparatus of claim 1 further comprising:
an instrument support extending distally of the coupled first and second pluralities of linkages.

12. The guiding apparatus of claim 1 further comprising:
a return assembly including a noncircular curved surface wherein the first plurality of linkages is configured to move along the noncircular curved surface of the return assembly.

13. The guiding apparatus of claim 1 further comprising:
a return assembly including a rotatable circular component and a ramping component, wherein the first plurality of linkages is configured to move along the ramping component and onto the rotatable circular component.

14. A method of guiding an interventional instrument, the method comprising:
receiving a portion of the interventional instrument through an opening of a continuous channel of a support assembly extending along a longitudinal axis and having a proximal end and a distal end, the support assembly including:
a first plurality of linkages including a first channel formation; and
a second plurality of linkages including a second channel formation, wherein in a coupled configuration, the first plurality of linkages is coupled to the second plurality of linkages with the first and second channel formations arranged to form the continuous channel;
advancing the proximal end of the support assembly in a first direction along the longitudinal axis;
separating a portion of the first plurality of linkages from a portion of the second plurality of linkages as a result of the interventional instrument advancing in the first direction along the longitudinal axis; and
directing the separated portions of the first and second pluralities of linkages away from the longitudinal axis.

15. The method of claim 14 wherein directing the separated portions of the first and second pluralities of linkages away from the longitudinal axis includes directing the separated portion of the first plurality of linkages away from the separated portion of the second plurality of linkages.

16. The method of claim 14 wherein directing the separated portions of the first and second pluralities of linkages away from the longitudinal axis includes directing the separated portions of the first and second pluralities of linkages in a second direction approximately opposite the first direction and approximately parallel to the longitudinal axis.

17. The method of claim 14 further comprising:
advancing a distal end of the interventional instrument distally beyond the separated portions of the first and second pluralities of linkages.

18. The method of claim 14 wherein:
the first channel formation of the first plurality of linkages forms a first undulated edge;
the second channel formation of the second plurality of linkages forms a second undulated edge;
the first and second undulated edges form the opening of the continuous channel; and
the portion of the interventional instrument is received in the opening of the continuous channel in a direction generally perpendicular to the longitudinal axis.

19. The method of claim 14 wherein separating the portion of the first plurality of linkages from the portion of the second plurality of linkages includes separating a first locking feature of each linkage of the first plurality of linkages from a corresponding second locking feature of each linkage of the second plurality of linkages.

20. The method of claim 14 wherein directing the separated portions of the first and second pluralities of linkages away from the longitudinal axis includes:
advancing the separated portion of the first plurality of linkages along a curved surface of a first return assembly; and
advancing the separated portion of the second plurality of linkages along a curved surface of a second return assembly.

* * * * *